(12) United States Patent
Hammon et al.

(10) Patent No.: US 7,118,654 B2
(45) Date of Patent: Oct. 10, 2006

(54) RISER BASE

(75) Inventors: Ulrich Hammon, Mannheim (DE); Juergen Schroeder, Ludwigshafen (DE)

(73) Assignee: BASF Aktiengesellschaft, Ludwigshafen (DE)

(*) Notice: Subject to any disclaimer, the term of this patent is extended or adjusted under 35 U.S.C. 154(b) by 82 days.

(21) Appl. No.: 10/495,130

(22) PCT Filed: Dec. 5, 2002

(86) PCT No.: PCT/EP02/13799

§ 371 (c)(1),
(2), (4) Date: May 20, 2004

(87) PCT Pub. No.: WO03/047714

PCT Pub. Date: Jun. 12, 2003

(65) Prior Publication Data

US 2005/0023125 A1    Feb. 3, 2005

(30) Foreign Application Priority Data

Dec. 6, 2001   (DE) ................. 101 59 825

(51) Int. Cl.
*B01D 3/32* (2006.01)

(52) U.S. Cl. .............. 203/57; 202/110; 202/158; 202/197; 261/114.1; 261/97; 562/545

(58) Field of Classification Search ........... 202/197, 202/158, 110; 261/114.1, 97; 562/545; 203/57
See application file for complete search history.

(56) References Cited

U.S. PATENT DOCUMENTS

| | | | |
|---|---|---|---|
| 3,855,068 A * | 12/1974 | Lieberman | 196/155 |
| 4,201,628 A | 5/1980 | Church et al. | |
| 4,698,138 A | 10/1987 | Silvey | |
| 4,933,047 A * | 6/1990 | Bannon | 202/197 |
| 5,338,517 A * | 8/1994 | Evans et al. | 422/191 |
| 5,567,396 A | 10/1996 | Perry et al. | |
| 5,972,171 A * | 10/1999 | Ross et al. | 203/40 |
| 6,372,944 B1 * | 4/2002 | Matsumoto et al. | 562/600 |
| 6,749,182 B1 * | 6/2004 | Larson et al. | 261/97 |
| 6,939,991 B1 * | 9/2005 | Thiel et al. | 562/545 |
| 2002/0098123 A1 * | 7/2002 | Matsumoto et al. | 422/100 |
| 2004/0129021 A1 * | 7/2004 | Thiel et al. | 62/617 |
| 2005/0006219 A1 * | 1/2005 | Eck et al. | 203/1 |
| 2005/0090628 A1 * | 4/2005 | Eck et al. | 526/67 |

FOREIGN PATENT DOCUMENTS

| | | |
|---|---|---|
| DE | 25 52 357 | 5/1977 |
| DE | 42 31 081 | 4/1993 |
| DE | 195 26 153 | 1/1996 |
| EP | 1 088 576 | 4/2001 |
| FR | 839 695 | 4/1939 |

* cited by examiner

*Primary Examiner*—N. Bhat
(74) *Attorney, Agent, or Firm*—Oblon, Spivak, McClelland, Maier & Neustadt, P.C.

(57) ABSTRACT

A chimney tray for a column for thermal treatment of a liquid. The chimney tray includes a total take-off of liquid by a drain connection arranged at an edge of the chimney tray, and having one or more drain channels having a gradient in a direction of the drain connection, and having a gradient in a direction of the one or more drain channels.

19 Claims, 2 Drawing Sheets

RISER BASE

The present invention relates to a chimney tray for a column for the thermal treatment of a liquid and a process for the thermal treatment in a column.

The present invention relates to chimney trays, i.e. a particular embodiment of column trays having chimneys for vapor passage which are covered by rigid hoods immersed in the liquid. Column trays are horizontally arranged plate-like components which are stiffened by U-profiles and are generally fastened—individually or as a plurality combined into a packet—to the column sidewall and are sealed liquid-tight from said sidewall (cf. K. Sattler: Thermische Trennverfahren, Verlag Chemie, 2nd Edition, 1995, page 194).

It is frequently necessary to remove some or all of the liquid occurring on the chimney trays in the rectification or absorption columns. For this purpose, the liquid can be taken off via a pipe connection by means of a pump after reaching a certain liquid height. However, owing to the large accumulation of liquid and the consequent long residence times for the treatment of thermally unstable substances, for example of (meth)acrylic acid and its esters, of acrylonitrile, styrene, etc., this method is unsuitable because of the tendency of said substances to polymerize.

A further method for removing liquid comprises equipping the chimney trays with an overflow weir, the liquid of the chimney trays flowing over this overflow of this weir into an externally arranged annular channel. The annular channel is tapped at one or more points along its circumference by means of pipe connections and the liquid is taken off. This embodiment, too, is problematic with substances having a high tendency to polymerize, since an uncontrolled polymerization takes place in the annular channel owing to a longer residence time and frequently high temperatures, so that the operability of the columns is adversely affected.

A large number of designs which ensure a reduced residence time of the liquid on column trays has therefore been proposed:

Thus, DE-A 42 31 081 describes a mass transfer tray having an integrated take-off facility for a liquid phase in the form of a take-off cup incorporated into a commercial mass transfer tray. The disadvantage here is that only a part of the liquid can be removed from the column tray.

EP-A 1 088 576 proposes a funnel-shaped column tray having a central liquid take-off via a pipeline. The disadvantage of this design is that, owing to the arrangement of the pipeline in the central lower region of the funnel-shaped tray, simple and effective isolation thereof, which would be required to reduce the thermal stress of the liquid present on the tray, is not possible.

DE-A 19526153 describes a chimney tray with total take-off and gradient in the form of an inverted cone. Here too, the central liquid take-off via a pipeline is disadvantageous.

It is an object of the present invention to provide a chimney tray having a minimized residence time of the liquid on the chimney tray and at the same time to reduce the thermal stress on the liquid on the chimney tray and hence its tendency to polymerize, by a procedure in which the chimney tray is isolated with minimum effort from underneath.

In addition, the undesired reflux of liquid through the chimneys and hence also the danger of polymerization are to be effectively prevented.

We have found that this object is achieved by a chimney tray for a column for the thermal treatment of liquid, comprising chimneys having hoods which are fastened to the chimneys by struts, and comprising take-off of the liquid via a drain connection arranged at the edge of the chimney tray.

In the present invention, the chimney tray has one or more drain channels having a gradient in the direction of the drain connection, and the chimney tray has a gradient in the direction of the drain channel or channels.

The present invention thus provides a chimney tray on which at least one drain channel for the liquid in the chimney tray is arranged. The drain channel or channels is or are in the form of a depression in the chimney tray. To ensure drainage of the liquid, a gradient is provided in two planes: on the one hand, a gradient of the chimney tray in the direction of the drain channel or channels and, on the other hand, a gradient of the drain channel in the direction of the drain connection. The drain connection may be arranged in any desired manner, for example in the middle or preferably at the edge of the chimney tray. A plurality of drain connections per discharge are of course also possible, for example 2, 3 or 4.

The gradient of the chimney tray to the drain channel is preferably from 0.5 to 5°, particularly preferably from 1 to 3°, and the gradient of the drain channel to the drain connection is from 0.2 to 5°, preferably from 0.5 to 2°.

The drain channel is preferably arranged in the middle of the chimney tray, i.e. it has a length corresponding to the diameter of the chimney tray. It is of course also possible to arrange a plurality, for example 2, 3 or 4, drain channels in the chimney tray so that the surrounding region of the chimney tray has a gradient to the respective drain channel.

The drain channel preferably has an arc-shaped profile. Its width, measured at the top of the chimney tray is preferably such that the ratio of the width of the drain channel to the diameter of the chimney tray is from 0.02 to 0.2, preferably from 0.05 to 1.

The chimney tray is preferably formed in such a way that it has a horizontal, flat bottom and an inclined top.

This design is preferably achieved by forming the bottom and the top in each case of metal sheets which are connected to one another by means of support and connecting elements, the drain channel being formed from a curved metal sheet which is connected, in particular welded, screwed or riveted, liquid-tight in a manner known per se to a person skilled in the art, to the top of the chimney tray.

In a preferred embodiment, the hoods of the chimneys are equipped with an edge which is bent downward. This facilitates the dripping of the liquid or reduces the undesired reflux of liquid on the underside of the hoods. Undefined liquid residence times and the danger of polymerization are avoided.

The width of the edge of the chimney hoods which is bent downward is preferably from 1 to 10, in particular from 2 to 6, cm.

The ratio b) of the diameter of the chimneys to the diameter of the chimney tray is preferably from 0.05 to 0.2, particularly preferably from 0.1 to 0.15.

The ratio c) of the distance from chimney center to chimney center to the diameter of the chimneys is preferably from 0.5 to 4, particularly preferably from 1 to 2.

The ratio d) of the height of the chimneys to the diameter of the chimneys is preferably from 0.5 to 5, particularly preferably from 1 to 3.

The hoods of the chimneys are preferably conical and have a gradient of from 5 to 30°, preferably from 10 to 20°. The number of struts for fastening a hood is preferably from 2 to 4, in particular 3.

Bubble caps, round, flat hoods having an edge which is bent downward or polygonal, planar hoods having an edge which is bent downward, for example in the case of Thormann trays, are also possible. The edge which is bent downward may also be serrated.

The ratio e) of the distance from the hoods without an edge which is bent downward to the upper end of the chimneys to the diameter of the chimneys is preferably from 0.1 to 1, in particular from 0.2 to 0.4.

A column comprising novel chimney trays is particularly suitable for the thermal treatment, preferably for the rectification or absorption, of fluid mixtures which contain thermally unstable compounds, in particular (meth)acrylic acid and/or its esters, for example acrylic acid, methyl, ethyl, n-butyl or 2-ethylhexyl acrylate, acrylonitrile and/or styrene. As customary, a gaseous and/or liquid mixture is defined as fluid.

The undesired polymerization in said processes for the thermal treatment can be further reduced by spraying in stabilized liquid taken off from the chimney tray, preferably from above onto the hoods and between the chimneys.

The present invention is described in more detail below with reference to the drawing.

Figure 1:
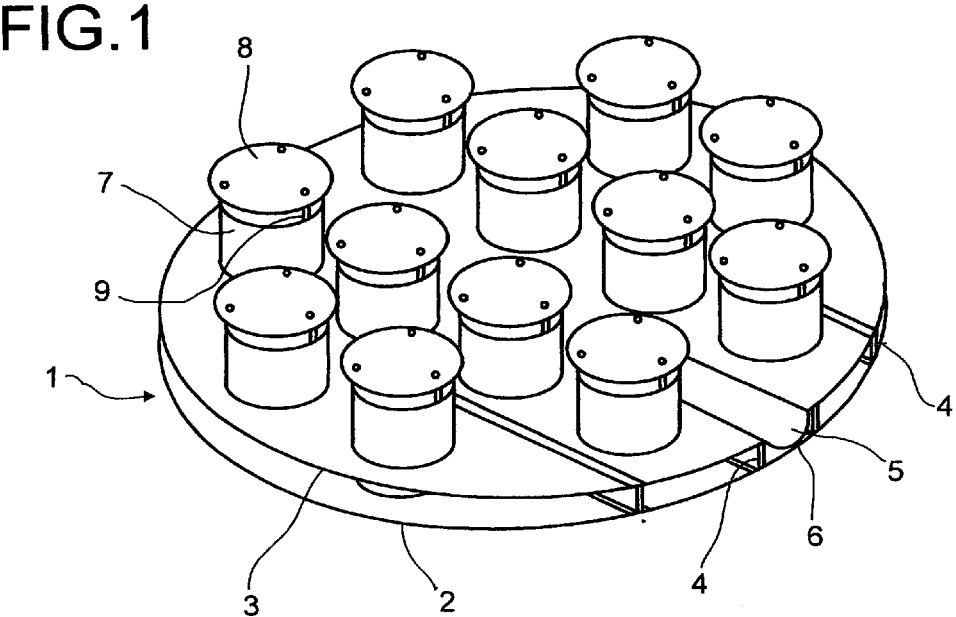
FIG. 1 shows the schematic diagram of an embodiment of a novel chimney tray.

The chimney tray 1 shown in FIG. 1 has a bottom 2 and a top 3 which are connected by means of support and connecting elements 4, with drain channel 5 arranged in the middle. A multiplicity of chimneys 7 having hoods 8 which are fastened by means of struts 9 are arranged on the chimney tray 1.

Figure 2:
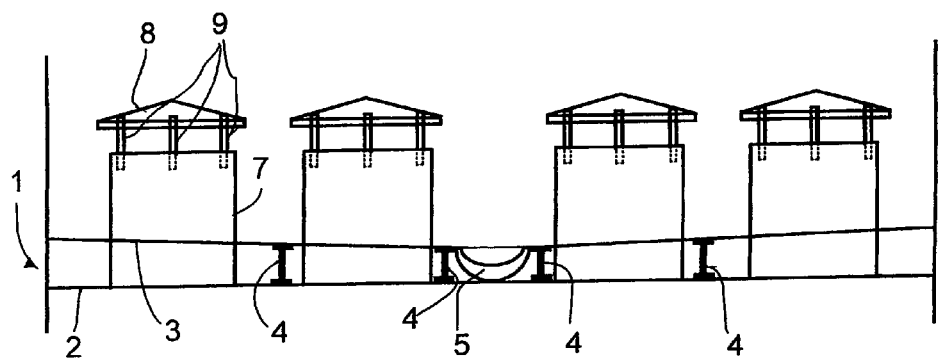
FIG. 2 shows a section through the chimney tray from FIG. 1, transversely to the drain channel.

The sectional diagram in FIG. 2 shows that the bottom 2 of the chimney tray is flat whereas the top 3 of the chimney tray is inclined in the direction of the drain channel 5. FIG. 2 also shows that the drain channel 5 itself is also inclined in the direction of the drain connection 6.

Figure 3:
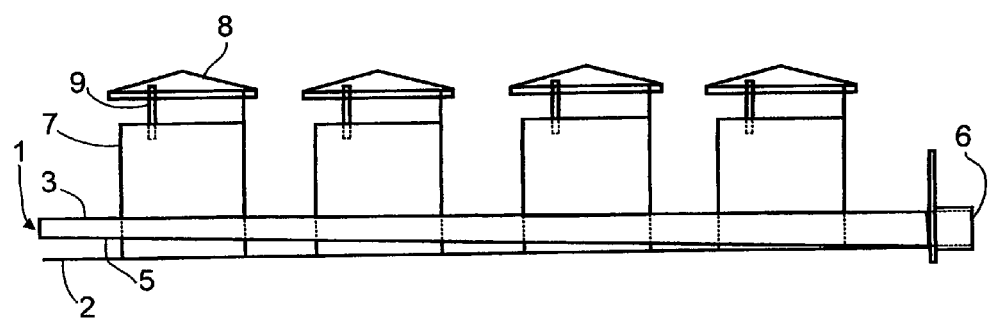
FIG. 3 shows a section through a chimney tray from FIG. 1, along the drain channel

The section shown in FIG. 3, in the longitudinal direction of the drain channel 5, shows the inclination thereof in the direction of the drain connection 6.

Figure 4:
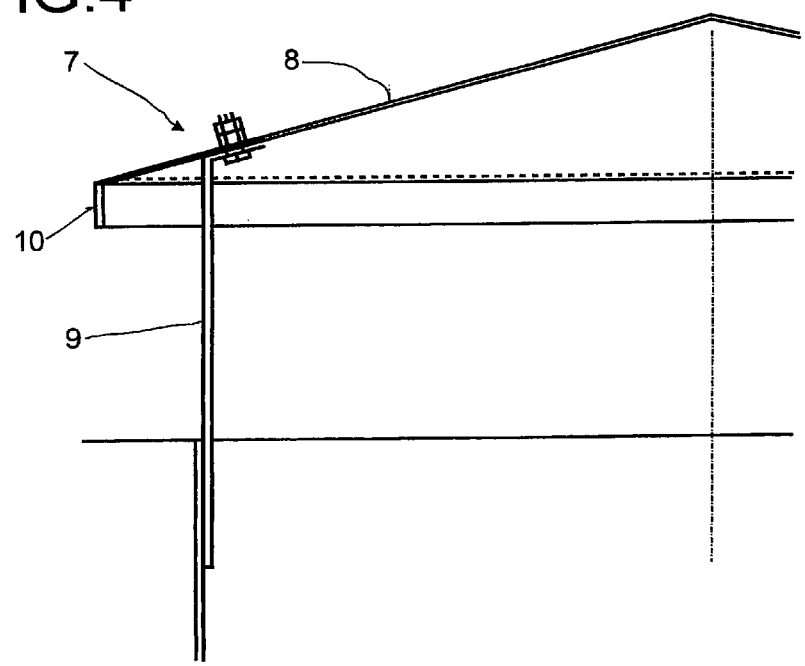
FIG. 4 shows a section through a chimney having a hood.

The sectional diagram through a chimney in FIG. 4 illustrates the edge 10 which is bent downward, at the lower end of the hood 8.

Embodiments:

An acrylic acid-containing reaction mixture was produced by catalytic gas-phase oxidation of acrolein according to example B1 of DE-A 43 02 991 and was further processed according to example 1 of DE-A 197 46 689.

The absorber column has a diameter of 6 m and 45 trays which are numbered beginning from the bottom. Trays 1, 14 and 35 were chimney trays corresponding to the schematic diagram in FIG. 1. The gradient of the drain channel (reference numeral 5 in FIG. 1) was 1° and the gradient of the chimney tray to the drain channel 5 was 2°.

After an on-stream time of 3 months, the chimney trays were inspected, with the following result:

| Tray 35 | No polymer |
| Tray 14 | about 5 kg of polymer |
| Tray 1 | about 20 kg of polymer |

For comparison, the experiment was repeated under analogous conditions but the chimney trays had no drain channel and no gradient.

After an on-stream time of 3 months, the chimney trays were inspected, with the following result:

| Tray 35 | about 5 kg of polymer |
| Tray 14 | about 70 kg of polymer |
| Tray 1 | about 250 kg of polymer |

We claim:

1. A chimney tray for a column for thermal treatment of a liquid, for a chimney having a hood that is fastened to the chimney with struts, comprising:
   take-off of the liquid by a drain connection arranged at an edge of the chimney tray, wherein the chimney tray has one or more drain channels having a gradient in a direction of the drain connection, and the chimney tray having a gradient in a direction of the one or more drain channels.

2. A chimney tray as claimed in claim 1, wherein the drain channel is arranged in a middle of the chimney tray.

3. A chimney tray as claimed in claim 1, wherein the gradient of the chimney tray to the one or more drain channels is from 0.5° to 5°, and the gradient of the one or more drain channels to the drain connection is from 0.2° to 5°.

4. A chimney tray as claimed in claim 3, wherein the gradient of the chimney tray to the one or more drain channels is from 1° to 3°, and the gradient of the one or more drain channels to the drain connection is from 0.5° to 2°.

5. A chimney tray as claimed in claim 1, wherein a ratio of a width of the one or more drain channels to a diameter of the chimney tray is from 0.02 to 0.2.

6. A chimney tray as claimed in claim 5, wherein the ratio of the width of the one or more drain channels to the diameter of the chimney tray is from 0.05 to 0.1.

7. A chimney tray as claimed in claim 1, having a horizontal, flat bottom and an inclined top.

8. A chimney tray as claimed in claim 7, wherein the bottom and the inclined top are each formed from metal sheets connected to one another by supports and connecting elements, and the one or more drain channels is formed from a curved metal sheet connected to the top of the chimney tray.

9. A chimney tray as claimed in claim 8, wherein the curved metal sheet is welded, screwed, or riveted liquid-tight to the top of the chimney tray.

10. A chimney tray as claimed in claim 1, comprising chimneys having hoods that are fastened to the chimneys with struts, wherein at least one of the hoods has an edge that is bent downward.

11. A chimney tray as claimed in claim 10, wherein a width of the edge of the at least one of the chimney hoods that is bent downward is from 1 to 10 cm.

12. A chimney tray as claimed in claim 11, wherein a width of the edge of the at least one of the chimney hoods that is bent downward is from 2 to 6 cm.

13. A chimney tray as claimed in claim 10, wherein at least one of the following relationships is provided: a ratio of a diameter of the chimneys to a diameter of the chimney tray is from 0.05 to 0.2, a ratio of a distance from chimney center to chimney center to the diameter of the chimney is from 0.5 to 4, and a ratio of a height of the chimneys to the diameter of the chimneys is from 0.5 to 5.

14. A chimney tray as claimed in claim 10, wherein at least one of the following relationships is provided: a ratio of a diameter of the chimneys to a diameter of the chimney tray is from 0.1 to 0.15, a ratio of a distance from chimney center to chimney center to the diameter of the chimney is from 1 to 2, and a ratio of a height of the chimneys to the diameter of the chimneys is from 1 to 3.

15. A chimney tray as claimed in claim 10, wherein at least one of the following is provided: the hoods are conical and have a gradient of from 5° to 30°, a number of struts for fastening a-heed at least one of the hoods is from 2 to 4, and a ratio of a distance from the hoods without the edge that is bent downward to an upper end of the chimney to the diameter of the chimneys is from 0.1 to 1.

16. A chimney tray as claimed in claim 15, wherein at least one of the following relationships is provided: the hoods that are conical have a gradient of from 10° to 20°, the number of the struts for fastening a-heed the at least one of the hoods is 3, and the ratio of the distance from the hoods without the edge that is bent downward to the upper end of the chimney to the diameter of the chimneys is from 0.2 to 0.4.

17. A process for thermal treatment of a fluid mixture in a column comprising chimney trays. each of the chimney trays as claimed in claim 11, wherein the fluid mixture contains thermally unstable compounds.

18. A process according to claim 17, wherein the thermal treatment is a rectification or absorption.

19. A process according to claim 17, wherein the thermally unstable compounds contained in the fluid mixture are (meth)acrylic acid and/or its esters, acrylonitrile, and/or styrene.

* * * * *